United States Patent [19]

Scholz et al.

[11] Patent Number: 5,273,971
[45] Date of Patent: Dec. 28, 1993

[54] 13-ALKYL-11β-PHENYLGONANES

[75] Inventors: Stefan Scholz; Eckhard Ottow; Guenter Neef; Walter Elger; Sybille Beier; Krzysztof Chwalisz, all of Berlin, Fed. Rep. of Germany

[73] Assignee: Schering Aktiengesellschaft, Berlin and Bergkamen, Fed. Rep. of Germany

[21] Appl. No.: 374,809

[22] Filed: Jul. 3, 1989

[30] Foreign Application Priority Data

Jul. 1, 1988 [DE] Fed. Rep. of Germany ....... 3822770

[51] Int. Cl.$^5$ ..................... A61K 31/58; C07J 43/00
[52] U.S. Cl. ................................. 514/176; 514/172; 514/173; 540/41; 540/106; 540/107; 540/108; 552/553; 552/520; 552/548; 552/554; 552/555; 552/556; 552/557; 552/504; 552/592; 552/593; 552/596; 552/598; 552/599; 552/608; 552/611; 552/645; 552/650; 552/646; 552/648
[58] Field of Search ............... 540/114, 116, 41, 44, 540/106, 107, 108; 514/172, 173; 552/553, 520, 548, 554, 555, 556, 557, 592, 593, 595, 598, 599, 608, 611, 645, 650

[56] References Cited

U.S. PATENT DOCUMENTS

| | | | |
|---|---|---|---|
| 3,971,772 | 7/1976 | Cimarusti et al. | 540/114 |
| 4,386,085 | 5/1983 | Teutsch et al. | 514/179 |
| 4,447,424 | 5/1984 | Teutsch et al. | 514/179 |
| 4,477,445 | 10/1984 | Philibert et al. | 514/460 |
| 4,519,946 | 5/1985 | Teutsch et al. | 540/76 |
| 4,540,686 | 9/1985 | Philibert et al. | 514/179 |
| 4,753,932 | 6/1988 | Teutsch et al. | 540/113 |
| 4,780,461 | 10/1988 | Neef et al. | 514/179 |
| 4,814,327 | 3/1989 | Ottow et al. | 514/179 |

FOREIGN PATENT DOCUMENTS

| | | |
|---|---|---|
| 52913 | 8/1986 | Australia . |
| 0057115 | 8/1982 | European Pat. Off. . |
| 0129499 | 12/1984 | European Pat. Off. . |
| 0190759 | 8/1986 | European Pat. Off. . |
| 0254670 | 1/1988 | European Pat. Off. . |
| 83/03099 | 9/1983 | World Int. Prop. O. . |

Primary Examiner—Thurman K. Page
Assistant Examiner—Jyothsna Venkat
Attorney, Agent, or Firm—Millen, White, Zelano, & Branigan

[57] ABSTRACT

There are provided 13-alkyl-11beta-phenyl-gonanes of formula I (I)

wherein
Z is an oxygen atom or N—OH;
$R^2$ is alpha- or beta-position methyl or ethyl;
$R^1$ is selected from heteroaryl radicals, cycloalkyl radicals, cycloalkenyl radicals, aryl radicals, alkenyl radicals, and alkyl radicals where $R^2$ is in the alpha-position and an ethyl radical where $R^2$ is in the beta-position; and
$R^3$ and $R^4$ are selected from one of two different groups of substituent pairs, the group from which the selection is made being determined by the position of $R^2$.

9 Claims, No Drawings

13-ALKYL-11β-PHENYLGONANES

BACKGROUND OF THE INVENTION

This invention relates to novel gonanes and the like, processes for producing same as well as starting materials, and methods of using compounds for their antigestagenic activity.

SUMMARY OF THE INVENTION

The present invention relates to 13-alkyl-11beta-phenyl-gonanes of the following general Formula I (I)

in which
Z stands for an oxygen atom or the hydroxyimino grouping N~OH,
$R^1$ stands either for
a) a heteroaryl radical of Formula Ia (Ia)

and A=N, O or S and
B—D—E mean the element sequence C—C—C, N—C—C or C—N—C or
b) a heteroaryl radical of Formula I b (Ib)

and A=N and
B—D—E mean the element sequence
C—C—C, N—C—C, C—N—C or C—C—N or
c) for a cycloalkyl, cycloalkenyl or aryl radical Ic or
d) for an alkenyl radical Id exhibiting straight-chain or branched, one or more double bonds with 2 to 10 carbon atoms and optionally the heteroaryl radicals of Formula Ia is substituted by one or more halogen radicals and/or one or more alkyl radicals with 1 to 3 carbon atoms
and the cycloalkyl, cycloalkenyl or aryl radical Id is substituted by one or more halogen, optionally protected hydroxy, alkoxy, oxidized alkylthio and/or dialkylamino radicals optionally in the form of the sulfoxide or sulfone and/or of the N-oxide and
$R^2$ stands for an alpha- or beta-position methyl or ethyl radical, and if $R^2$ is in alpha position,
$R^1$ stands additionally for a straight-chain or branched alkyl radical with 1 to 10 carbon atoms and $R^3/R^4$ mean $-OR_5/-C\equiv CY\ -H/-\underset{\underset{O}{\|}}{C}-CH_2R_6$ $-C\equiv CY/-OR_5\quad -\underset{\underset{O}{\|}}{C}-CH_2R_6/H$ $-OR_5/-\underset{\underset{O}{\|}}{C}-CH_2R_6\quad -OR_5/(CH_2)_o-CH_2R_7$ $-\underset{\underset{O}{\|}}{C}-CH_2R_6/-OR_5\quad -(CH_2)_o-CH_2R_7/-OR_5$ $-CH_3/-\underset{\underset{O}{\|}}{C}-CH_2R_5\quad -OR_5/-CH=CH-(CH_2)_kCH_2R_7$ $-\underset{\underset{O}{\|}}{C}-CH_2R_6/-CH_3\quad -CH=CH-(CH_2)_kCH_2R_7/-OR_5$ $-OR_5/-H$ $-H/-OR_5$ and if $R^2$ is in beta position
$R^1$ additionally stands for an ethyl radical, but $R^1$ cannot be the alkenyl radical isopropenyl and $R^3/R^4$ mean $-OR_5/C\equiv CY\quad \underset{\underset{O}{\|}}{C}-CH_2R_6/-H$ $-OR_5/-\underset{\underset{O}{\|}}{C}-CH_2R_6\quad -OR_5/-(CH_2)_a-CH_2R_7$ $-\underset{\underset{O}{\|}}{C}-CH_2R_6/-OR_5\quad -OR_5/-CH=CH-(CH_2)_kCH_2R_7$ $-OR_5/-H$
$-\underset{\underset{O}{\|}}{C}-CH_2R^6/-CH_3$ with $R_5$ in the meaning of a hydrogen atom or an acyl radical with 1 to 4 carbon atoms.
Y in the meaning of a hydrogen, chlorine, fluorine, iodine or bromine atom, an alkyl, hydroxyalkyl, alkoxyalkyl or acyloxyalkyl group each with 1 to 4 atoms in the alkyl or acyl radical,
$R_6$ in the meaning of a hydrogen atom, a hydroxy group, an alkyl, 0-alkyl or 0-acyl group each with 1 to 4 carbon atoms, o in the meaning of 0, 1, 2 or 3,
$R_7$ in the meaning of a hydroxy or cyanide radical, an 0-alkyl or 0-acyl group each with 1 to 4 carbon atoms and k in the meaning 0, 1 or 2, Process for their production, pharmaceutical preparations containing these compounds as well as the new starting materials and intermediate products and processes for their production.

Among the heteroaryl radicals possible according to Formula Ia, the 3-thienyl, 3-furyl and 3-pyrrole radicals are preferred.

As heteroaryl radical of Formula Ib, according to the invention the 3-pyridyl or 4-pyridyl, the 5-pyrimidine, 4-pyridazine or pyrazine radicals are especially suitable.

As cycloalkyl, cycloalkenyl or aryl radical Ic, the cyclohexyl, cyclohex-1-enyl, cyclohex-2-enyl-, cyclohex-3-enyl-, as well as the phenyl radical are to be especially emphasized.

Alkenyl radical Id preferably is to exhibit up to 3 double bonds.

As halogen substituents that are possible in the heteroaryl radical of Formula Ia, a chlorine or bromine atom are especially to be named.

If the heteroaryl radical of Formula Ia is alkyl substituted, then monosubstitution is preferred.

Cycloalkyl, cycloalkenyl or aryl radical Ic can be substituted by one or two chlorine and/or bromine atom(s). The radicals named can also be substituted by one or two, optionally protected hydroxy and/or alkoxy radicals with 1 to 8 carbon atoms.

The compounds of general Formula I have a strong affinity for the gestagen receptor, without themselves developing gestagen activity. They are competitive antagonists of the progesterone (antigestagens); since they displace from the receptor the progesterone necessary for maintaining pregnancy, they are suitable for triggering abortions and for inducing birth.

In addition to the named indications, the compounds according to the invention can also be used for treatment of endometriosis, dysmenorrhea and hormone-associated tumors, such as e.g., breast cancer and durosarcoma.

To characterize the antigestagen effect of the compounds according to the invention, the abortive effectiveness was determined. The tests were performed on female rats with a weight of about 200 g. After successful mating, the start of pregnancy was checked by detection of sperm in vaginal smears. The day of the sperm detection counts at day 1 of pregnancy (=d 1 p.c.).

The treatment of the animals with the substance to be tested in each case or with the solvent was performed on d. 5 to d. 7 p.c.

On d. 9 p.c., the animals were killed and the uteri were examined for nidations and absorptive points. The lack of nidations was considered an abortion.

As antigestagens there were studied:

A: 17alpha-(3-hydroxyprop-1-(Z)-enyl)-17beta-hydroxy-11beta-(4-vinylphenyl)-4,9-estradien-3-one B: 17alpha-(prop-1-inyl)-17beta-hydroxy-11beta-(4-vinylphenyl)-4,9-estradien-3-one C: 17beta-(3-hydroxypropyl)-17alpha-hydroxy-13alpha-methyl-11beta-(4-isopropenylphenyl)-4,9-gonadien-3-one D: 11beta-(4-ethylphenyl)-17-hydroxy-17beta-(3-hydroxypropyl)-13alpha-methyl-4,9-gonadien-3-one E: 17-hydroxy-17beta-(3-hydroxypropyl)-13alpha-methyl-11beta-(4-vinylphenyl)-4,9-gonadien-3-one F: 17-hydroxy-17alpha-(3-hydroxyprop-(Z)-1-enyl)-11beta-[4-(3-pyridyl)-phenyl]-4,9-estradien-3-one G: 17-hydroxy-17beta-(3-hydroxypropyl)-13alpha-methyl-11beta-[4-(3-pyridyl)-phenyl]-4,9-gonadien-3-one H: 17-hydroxy-17beta-(3-hydroxypropyl)-13alpha-methyl-11beta-[4-(2-thiazolyl)-phenyl]-4,9-gonadien-3-one I: 17-hydroxy-17alpha-(3-hydroxy-(Z)-1-enyl)-11beta-[4-(3-thienyl)-phenyl]-4,9-estradien-3-one K: 17-hydroxy-17beta-(3-hydroxypropyl)-13alpha-methyl-11beta-[4-(3-furyl)-phenyl]-4,9-gonadien-3-one L: 17-hydroxy-17beta-(3-hydroxypropyl)-13alpha-methyl-11beta-[4-(3-thienyl)-phenyl]-4,9-gonadien-3-one M: 17-hydroxy-17alpha-(3-hydroxyprop-(Z)-1-enyl)-11beta-[4-(3-furyl)-phenyl]-4,9-estradien-3-one N: 17-hydroxy-17beta-3-hydroxypropyl)-13alpha-methyl-11beta-(4-cyanophenyl)-phenyl]-4,9-gonadien-3-one O: 17-hydroxy-17beta-(3-hydroxypropyl)-13alpha-methyl-11beta-[4-(5-pyrimidyl)-phenyl]-4,9-gonadien-3-one P: 17-hydroxy-17alpha-(3-hydroxyprop-(Z)-1-enyl)-11beta-[4-(2-thiazolyl)-phenyl]-4,9-estradien-3-one Q: 11beta-[4-(dimethylamino)phenyl]-17beta-hydroxy-17alpha-(propion-1-yl) 4,9(10)-estradien-3-one, RU-486 (EP-A 0057115).

The test substances were dissolved in a benzyl benzoate castor oil mixture (1:4 ratio). The treatment was performed subcutaneously (s.c.).

The results are presented in Table 1.

TABLE 1

Abortive effect of compounds (A) to (P) according to the invention in an early phase of pregnancy of rats. Treatment between d.5 p.p. and d.7 p.c., autopsy on d.9 p.c.

| Compound | Dose (mg/animal/day s.c.) | Abortion rate n abortions/ n/total |
|---|---|---|
| A | 3.0 | 4/4 |
|   | 1.0 | 4/4 |
|   | 0.3 | 2/4 |
| B | 3.0 | 4/4 |
|   | 1.0 | 3/4 |
|   | 0.3 | 0/4 |
| C | 3.0 | 4/4 |
|   | 1.0 | 0/4 |
| D | 3.0 | 3/4 |
|   | 1.0 | 0/4 |
| E | 3.0 | 3/4 |
|   | 1.0 | 0/4 |
| F | 3.0 | 4/4 |
|   | 1.0 | 4/4 |
|   | 0.3 | 0/4 |
| G | 3.0 | 4/4 |
|   | 1.0 | 4/4 |
|   | 0.3 | 4/4 |
|   | 0.1 | 0/4 |
| H | 3.0 | 4/4 |
|   | 1.0 | 3/4 |
|   | 0.3 | 0/4 |
| I | 3.0 | 4/4 |
|   | 1.0 | 4/4 |
|   | 0.3 | 0/4 |
| K | 3.0 | 4/4 |
|   | 1.0 | 4/4 |
|   | 0.3 | 4/4 |
|   | 0.1 | 0/4 |
| L | 3.0 | 4/4 |
|   | 1.0 | 4/4 |
|   | 0.3 | 0/4 |
| M | 3.0 | 4/4 |
|   | 1.0 | 4/4 |
|   | 0.3 | 4/4 |
|   | 0.1 | 4/4 |
| N | 3.0 | 4/4 |
|   | 1.0 | 4/4 |
|   | 0.3 | 0/4 |
| O | 3.0 | 4/4 |

TABLE 1-continued

Abortive effect of compounds (A) to (P) according to the invention in an early phase of pregnancy of rats. Treatment between d.5 p.p. and d.7 p.c., autopsy on d.9 p.c.

| Compound | Dose (mg/animal/day s.c.) | Abortion rate n abortions/ n/total |
|---|---|---|
|   | 1.0 | 4/4 |
|   | 0.3 | 0/4 |
| P | 3.0 | 4/4 |
|   | 1.0 |   |
|   | 0.3 |   |
| Q | 3.0 | 4/4 |
|   | 1.0 | 2/4 |
|   | 0.3 | 0/4 |
| Solvent as control: |   | 0/4 |
| 0.2 ml of benzyl benzoate + castor oil (1:4) |   |   |

If for R¹ *in the 13alpha-methyl series stands a 3-pyridyl* residue (G) or 3-furyl residue (K) or in the 13beta-methyl series a 3 furyl residue (M), the compounds according to the invention show very strong efficiency; especially the substitution with a 3-furyl residue in the 13beta-series is to be emphasized: the tested compound M is even in a dose of 0.1 mg/animal/day still fully effective whereas compound Q which is to be regarded as a standard compound is totally ineffective already in a dose of 0.3 mg/animal/day.

| N | 3.0 | 4/4 |
|---|---|---|
|   | 1.0 |   |
|   | 0.3 |   |
| O | 3.0 | 4/4 |
|   | 1.0 |   |
|   | 0.3 |   |
| P | 3.0 | 4/4 |
|   | 1.0 |   |
|   | 0.3 |   |
| Solvent as control: |   | 0/4 |
| 0.2 ml of benzyl benzoate + castor oil (1:4) |   |   |

To characterize the antiglucocorticoid effect, the influence of the substances according to the invention on tyrosineaminotransferase was determined. The test system is based on a measurement of the activity of the liver enzyme tyrosine aminotransferase (TAT) in cultures of RHC (rat hepatoma cells). The enzyme catalyzes the first step in the metabolization of tyrosine and can be induced in the liver as well as in hepatoma cells by glucocorticoids. The activity is easily measured in crude extracts (Granner and Tomkins, (1970) Meth. Enzymol. 15, 533). The enzyme converts the amino group of tyrosine into 2-oxoglutaric acid. In doing so, glutamic acid and p-hydroxyphenylpyruvate are produced. In alkaline solution, from p-hydroxyphenylpyruvate there is formed the more stable p-hydroxybenzaldehyde, whose absorption is measured at 331 nm. The TAT activity in RHC cells shows a dose-dependent induction with cortisol (max. act. at $10^{-6}$M) or dexamethasone (max. act. at $10^{-7}$M). The activity can be stimulated above the basal value by a factor of 4-6. Simultaneous treatment with corticoid and antiglucocorticoid leads to a reduction of the TAT activity.

Compounds A and E according to the invention show, in this test, about 1%, compounds F and G about 2%, compound D about 5% and compound B about 100% of the activity of 11beta-[4-dimethylaminophenyl)-17beta-hydroxy-17alpha-(prop-1-inyl)-4,9-estradien-3-one RU 486 [B], a substance that is to be considered standard (7th Int. Congress of Endocrinology July 1-7, 1984, Quebec City, Canada: Excerpts Medica, Amsterdam-Oxford-Princeton).

The compounds according to the invention of general formula I can be used in the form of pharmaceutical preparations. The production of the preparations is performed according to galenic methods known in the art by mixing with organic or inorganic, inert carrier material that is suitable for enteral, percutaneous or parenteral administration.

The dosage of the compounds according to the invention for the indications given is between 1 and 1,000 mg daily.

The 13-alkyl-11beta-phenylgonanes of general formula I, in which the 11beta-phenyl radical in 4 position carries the substituents according to the invention, are produced according to the process according to claim 11.

In doing so, a compound of general formula II

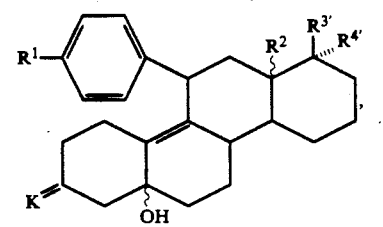

in which K means a blocked keto group in the form of ketal, thioketal, oxime or methyloxime, $R^1$ and $R^2$ have the above-mentioned meaning and $R^3$ and $R^4$ have the same meaning as $R^3$ or $R^4$, and hydroxy groups optionally present in $R^3$ and hydroxy and/or acyl groups optionally present in $R^4$ are protected, with the effect of a dehydration agent that is capable of releasing the protected function(s), is subjected to water separation with formation of 4(5) double bonds, is again protected in cycloalkyl, cycloalkenyl or aryl radical Id, alkylthio and/or dialkylamino radicals optionally present in radical Id are oxidized optionally to the corresponding sulfoxide, sulfone and/or N-oxide and then reacted optionally with hydroxylamine hydrochloride in the presence of tertiary amines at temperatures between $-20°$ C. and $+40°$ C.

The acidic treatment is performed in a way known in the art in that the compound of Formula II, which contains at least two protective groups, is dissolved in a solvent miscible with water such as aqueous methanol, ethanol or acetone and catalytic amounts of mineral or sulfonic acid such as hydrochloric acid, sulfuric acid, phosphoric acid, perchloric acid or p-toluenesulfonic acid, or an organic acid, such as acetic acid, are left to act on the solution until water is separated and protective groups are removed. The reaction that occurs at temperatures of $0°-100°$ C., can also be performed with an acidic ion exchanger. The course of the reaction can be followed with analytical methods, for example by samples taken by thin film chromatography.

To produce the compounds of general Formula II, there exist various possibilities according to the invention.

In one variant, starting from a compound of general Formula III

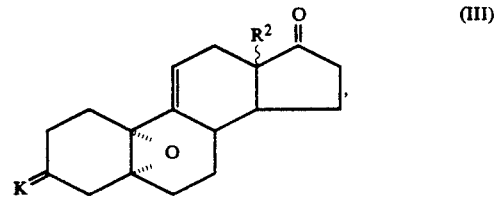

the latter is reacted, according to the usual processes of the C17 side chain build-up by introduction of substituents R³ and R⁴ by nucleophilic addition to the C17 ketone and subsequent reactions ("Teipenoids and Steroids", Specialist Periodical Report, The Chemical Society, London, Vol. 1-12) into a compound of general Formula IV

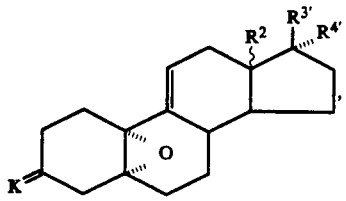

(IV)

Access to the 13alpha-methyl-or 13alpha-ethyl series (R₂ is in alpha position) is performed—such described, e.g., in European patent application 0259 248—by irradiation of intermediate products of general Formula III (Tetrahedron Letters 26, 2069 (1985), R₂ is in beta position) with ultraviolet light.

While the nucleophilic addition to the 17-ketone of the 13beta-alkyl series yields only adducts with the hydroxy group in beta position and the entering group in the alpha position to the five-membered ring, the addition to the corresponding 13-epi-17-ketone occurs generally with the formation of both possible isomeric forms at C-17 which, however, are easily separated by chromatography or fractionated crystallization. In many cases, both isomers are pharmacologically effective, even if differences can exist in the strength of the effect.

The nucleophilic addition of HC≡CX in which X means hydrogen, alkyl with 1-4 C atoms or halogen, is performed with the aid of a compound of general formula MC≡CX, in which X has the meaning indicated above and M represents an alkaline metal.

The metallo-organic compound can also be formed in situ and brought to reaction with the 17-ketone. Thus, for example there can be left to react on the 17-ketone, in a suitable solvent, acetylene and an alkaline metal, in particular potassium, sodium or lithium, in the presence of an alcohol or in the presence of ammonia. The alkaline metal can also be used in the form of, for example, methyl or butyl lithium. As solvents, dialkylether, tetrahydrofuran, dioxan, benzene and toluene are suitable in particular.

To produce the 17-chloroethinyl compound, the metallo-organic chloroethinyl compound is formed in situ from 1,1-dichloroethylene and an ethereal alkaline metal solution, such as for example methyl or butyl lithium solution and is reacted with the 17-ketone in solvents, such as tetrahydrofuran or diethylether.

The 17-ethinyl-17-hydroxy compounds can be hydrated in alcoholic solution with mercury salt catalysis into the 17-actyl-17-hydroxy compounds (Chem. Ber. [Chemical Reports] 111, (1978), 3086-3093).

The introduction of 3-hydroxypropine, propene or propane into the 17 position is performed by reaction of the 17-ketone with metallized derivatives of propargyl alcohol, for example with 1-lithium-3-tetrahydropyran-2'-yloxy-propine-1 into the 17-(3-hydroxy-1-propinyl)-17-hydroxy compounds, which can then be hydrogenated into the 17-(3-hydroxypropyl or 3-hydroxypropenyl)-17-hydroxy compounds. The hydrogenation must be performed under conditions that guarantee exclusively attack on the C—C triple bond, without saturating the optionally present tetrasubstituted 9(10) double bond. This succeeds, for example, with hydrogenation at room temperature and normal pressure in solvents such as methanol, ethanol, propanol, tetrahydrofuran (THF) or acetic ester with the addition of noble metal catalysts such as platinum or palladium.

The introduction of the homologs hydroxyalkyne, hydroxyalkene and hydroxyalkane groups is performed in a suitable way with homologs of propargyl alcohol.

The compound with the Z configured double bond in the hydroxypropenyl group is produced by hydrogenation of the acetylenic triple bond with a deactivated noble metal catalyst (J. Fried, J. A. Edwards: Organic Reactions in Steroid Chemistry, Van Nostrand Reinhold Company 1972, page 134 and H. O. House: Modern Synthetic Reactions 1972, page 19). As deactivated noble metal catalysts, for example 10% palladium on barium sulfate in the presence of an amine or 5% palladium on calcium carbonate with the addition of lead(II) acetate are suitable. The hydrogenation is interrupted after the absorption of an equivalent hydrogen.

The compound with the E-configured double bond in the hydroxypropenyl group is produced by reduction of the acetylenic triple bond in a way known in the art. In the literature there are described a whole series of methods for converting alkynes into trans-olefins, for example the reduction with sodium in liquid ammonia (J. Am. Chem. Soc, 63 (1941) 216), with sodium amide in liquid ammonia (J. Chem. Soc., 1955, 3558), with lithium in low molecular amines (J. Am. Chem. Soc. 77 (1955) 3378), with boranes (J. Am. Chem. Soc. 93 (1971) 3395) and 94 (1971 (6560), with diisobutylaluminum hydride and methyllithium (J. Am. Chem. Soc. 89 (1967) 5085) and in particular with lithium aluminum hydride/alcoholate (J. Am. Chem. Soc. 89 (1967) 4245). Another possibility is the reduction of the triple bond with chromium(II)-sulfate in the presence of water or dimethylformamide in a slightly acidic environment (J. Am. Chem. Soc. 85 (1964) 4358) as Well as generally the reduction by the action of transition metal compounds with alternation in the oxidation step.

If end products of Formula I are desired with R₃/R₄ in the meaning of

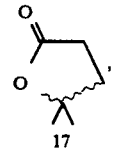

then 17-(3-hydroxypropyl) compound is oxidized in a way known in the art, for example with Jones reagent, manganese dioxide, pyridinium dichromate, pyridinium chlorochromate, chromic acid-pyridine or with the Fetizon reagent silver carbonate/celite (Compt. Rend. 257 (1968) 900).

To introduce the grouping

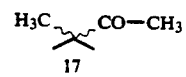

the 17 ketone is converted with tosylmethylisocyanide into the 17-nitrile compound, from the 17-nitrile compound there is obtained, with methyllithium or methyl-magnesium bromide, the 17-acetyl compound which, after enolization with K-tert.-butylate in tetrahydrofuran and reaction with methyl iodide, yields the desired grouping in 17 position.

The formation of the 17-cyanomethyl side chain is performed in a way known in the art from the 17-ketone, for example by the 17-spiro epoxide and cleavage of the spiro epoxide with HCH according to Z. Chem. 15, (1978) 259-260.

The introduction of the 17-hydroxyacetyl side chain is also performed according to methods known in the art, for example according to the methods described in J. Org. Chem. 47, (1982), 2993-2995.

Free hydroxy groups in the 17 position can be esterified or etherified in a way known in the art.

The compounds of general formula IV are then reacted, by Grignard addition of an aryl Grignard compound that already carries in the 4 position the desired substituent $R^1$, into a compound of general Formula II that is further processed in the way already indicated.

But according to the invention it is also possible to react a compound of general formula IV with a compound of the type $(H_{2m+1}C_m)_3Sn$—⟨phenyl⟩—W, in which W means MgX (X=Br, I) or preferably Li (S. H. Lee, R. N. Hanson and D. E. Seitz, Tetrahedron Letters 25, 1751 (1984) and m 1,2,3,4, preferably 1 or 4, with generation of a compound of general formula V (V)

in which K, $R^2$, $R^3$ and $R^4$ have the meaning already indicated (K. Torssell, J. Goldman, T. E. Petersen: Liebigs Ann. Chem. 1973, 231-240).

From such a compound, the compound of general formula II is obtained in a Pd (0) catalyzed reaction in the presence of an $R^1Br$ compound, in which $R^1$ is the substituent $R^1$ desired in the end product.

If a compound of general formula II is to be produced in which substituent $R^2$ is exclusively in alpha position, one can proceed so that a compound of general formula IV ($R^2$=alpha position) is brought to reaction with a Grignard adduct of formula Br—⟨phenyl⟩—MgX (X = Br, I)

and the reaction product of general formula VI (VI)

in which K, $R^2$, $R^{3'}$ and $R^{4'}$ have the meaning indicated above is further reacted to introduce the $R^1$ substituent into the 4 position of the 11beta configured phenyl ring in the presence of catalytic amounts of Pd(0) with a tin organic compound of general formula $R^1Sn(C_mH_{2m+1})_3$ (J. K. Stille. Angew. Chem. [Applied Chemistry] 96 (1986) 504-519) into the corresponding compound of general formula II (II)

Instead of the variant just mentioned, it is also possible to react a compound of general formula VI, first palladium(0) catalyzed with a hexaalkyldistannane $[C_mH_{2m+1})_3Sn]_2$ (m=1,2,3,4, preferably 1 or 4) into a compound of general formula V and to further process the latter—as already indicated—into a compound of general formula II (Y. Yamamoto, Y. Azuma, H. Mitoh, Communications, pages 564-565, 1986, T. J. Bailey, Tet. Let., 27, pages 4407-4410, 1986.

The intermediate products of general formulas III to VI occurring according to claim 12 during the course of possible synthesis routes to the initial products of general formula II can all be isolated in substance and also count as part of the object of this invention.

Common to all process variants described above is the fact that into the C17-keto compound of general Formula III there are first introduced, by nucleophilic addition, the precursors $R^{3'}$, $R^{4'}$ of the $R^3$ and $R^4$ substituents or these two substituents themselves, with formation of a compound of general Formula IV and that only afterwards is the 11beta-phenyl radical with the corresponding substitution pattern established in the 4 position.

In contrast to this, according to the invention the synthesis of the compounds of general formula I can also be started with a 13beta-alkyl-5,10-epoxide of general Formula VII (VII)

which K and R² have the meaning indicated further above, in that into the latter there is first introduced a phenyl radical that exhibits, in the 4 position, the labile tin trialkyl group (alkyl, $C_1-C_4$), preferably $C_1$ or $C_4$) by Grignard addition of a suitable 4-(trialkylstannyl)-aryl Grignard compound or alkylation with a 4-(trialkylstannyl)-aryllithium compound with formation of a compound of general formula VIII

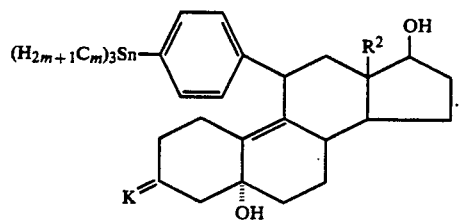
(VIII)

From a compound of general formula VIII, by coupling, which is transition metal-catalyzed, preferably Pd(0)-catalyzed, with a compound $R^1$-Y(Y - Br, I) there is reached a compound of general formula IX

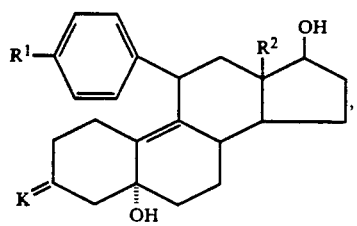
(IX)

next by oxidation of the 17beta-OH function and optionally subsequent irradiation with ultraviolet light (conversion of the 13beta-alkyl into a 13alpha alkyl group) there is reached a compound of general formula X

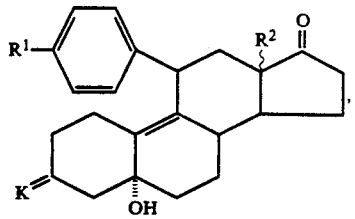
(X)

in which the substituents have the meanings already indicated and R² can be in alpha as well as beta position, into which then the R³ and R⁴ substituents are introduced in the way already described by nucleophilic addition and they are separated from the protective groups present by acidic treatment with the release of a compound according to the invention of general formula I.

The sequence of the reaction steps described here, running through the compounds of formulas IX and X, starting from a compound of formula VIII can, starting from the same compound VIII, also be switched, in that first the 17beta-OH is oxidized into the corresponding 17-keto function, next optionally it is irradiated with ultraviolet light and then, by transition metal-catalyzed, preferably Pd(O)-catalyzed coupling with a compound $R^1$-Y (Y=Br, I), the intermediate compound already described above of general formula X is generated, which is then reacted—also as already described—into a compound of formula I. In doing so, a compound of general formula XI is passed through

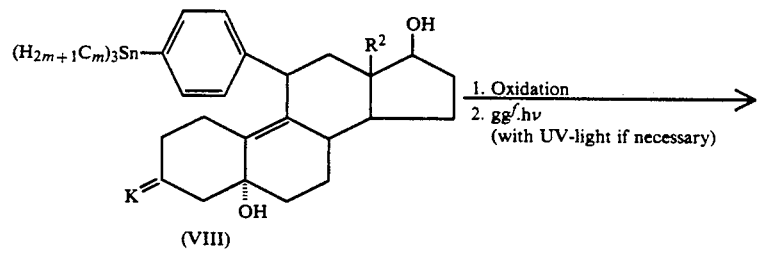
(VIII)

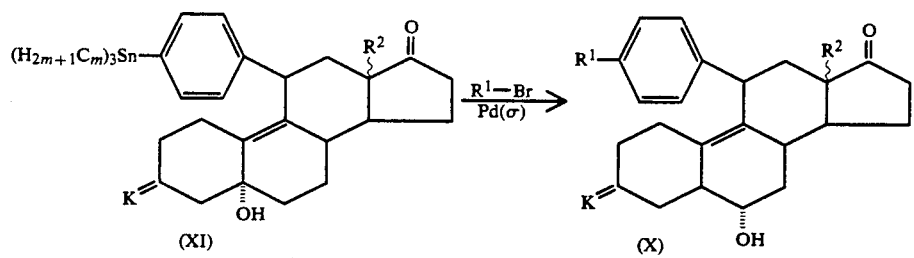
(XI)    (X)

In a compound of general formula (XI) nucleophilic addition can also be first performed to the C-17 atom to establish the radicals R³ and R⁴ or their precursors R³' and R⁴' with formation of a compound of general formula V which then, as already indicated, is further to be processed.

The compounds of general formulas VIII to XI, just as those of formulas III to VI, can also be isolated in substance and belong to the object of this invention.

The following representative examples serve to explain the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents and publications, if any, cited above and below, and of corresponding application P 38 22 770.3 filed Jul. 1, 1988 in the Federal Republic of Germany, are hereby incorporated by reference.

General Directions for Producing the Compounds of General Formula I by Acidic Splitting of the Compounds of General Formula II Table 2

A solution of x g of a steroid of general formula II in y ml of 70% acetic acid is stirred for z minutes at t°C. Next, the reaction mixture is poured on ice water, neutralized by adding aqueous ammonia solution and extracted with dichloromethane. The combined organic phases are washed with a saturated common salt solution, dried over sodium sulfate and concentrated by evaporation in a vacuum. By chromatography on silica gel with a mixture of ethyl acetate/hexane, a g of the desired compound of general formula I is obtained from the raw product.

General Directions for Production of the Compounds of General Formula II

A) By Grignard Addition

Table 3

10.6 mmol of magnesium chips is first placed under protective gas in 5 ml of absolute tetrahydrofuran and mixed with 0.8 mmol of dibromoethane. After completed reaction, a solution of 10 mmol of haloaromate is slowly instilled in 11 ml of absolute tetrahydrofuran. After complete reaction, the Grignard solution is cooled to 0° C. and mixed with 0.28 mg of copper-(I)-chloride. Next a solution of 12 mmol of epoxide EP is instilled in 7.5 ml of absolute tetrahydrofuran. The reaction mixture is warmed slowly overnight to room temperature and then poured over saturated ammonium chloride solution. The aqueous phase is extracted with ethyl acetate, the organic phases are combined, washed with saturated common salt solution and dried over sodium sulfate. After concentration by evaporation in a vacuum, the residue is chromatographed on aluminum oxide (Merck, Step III, neutral) with a mixture of ethyl acetate/hexane. Finally, y mmol of the desired adduct Y is isolated as a white foam.

B) By coupling Steroid Stannanes of General Formula V with Arylbromides (Table 4)

2.27 mmol of stannyl steroid is placed in 60 ml of absolute dioxane under protective gas, mixed consecutively with 27.1 mmol of arylbromide as well as 0.228 mmol of bis-(triphenylphosphine)-palladium(II)-chloride and refluxed 24 hours. The reaction mixture is filtered over belite, rewashed with ethyl acetate and mixed with the same volume of a 10% ammonia solution. After 30 minutes of stirring, the organic phase is separated, washed with saturated NaCl solution and dried. After concentration by evaporation in a vacuum, the residue is chromatographed on aluminum oxide (Merck, Step III, neutral) with a mixture of ethyl acetate/hexane. A g of the desired compound of general formula II is obtained (Table 4).

C) By Coupling Bromosteroids of General Formula VI with Heteroaryl Stannanes (Preparation Analogous to Lit. Ue. Organometal. Chem., 246(1983)163). [Table 5]

2.23 mmol of bromosteroid is placed in 50 ml of absolute dioxane, mixed consecutively with 22.3 mmol of arylstannane as well as 0.228 mmol of bis-(triphenylphosphine)-palladium(II)chloride and refluxed for 2 hours. After the working up described under a), b g of the desired compound of general formula II is obtained (Table 5).

EXAMPLE 1

17-(prop-1-inyl)-17beta-hydroxy-11beta-(4-vinylphenyl)-4,9-estradien-3-one

Table 2 a) Production of the starting substrate for the Grignard addition 17-(prop-1-inyl)-5alpha, 10alpha-epoxy-3,3-(2,2-dimethyltrimethylenedioxy)-9(11)-estrene-17beta-ol 1.3 l of absolute tetrahydrofuran is saturated at 0° C. by introducing propine with this gas. Next the solution is cooled down to −10° C. and mixed slowly with 166 ml of a 1.6 m solution of n-butyllithium in hexane. After 15 minutes of restirring at 0° C., a solution of 8.9 g of 5alpha, 10alpha-epoxy-3,3-(2,2-dimethyltrimethylenedioxy)-9(11)-estren -17-one is instilled in 250 ml of absolute tetrahydrofuran. After the addition, the reaction mixture is stirred for another 30 minutes at 0° C. and then poured over ice water. The aqueous phase is extracted with ethyl acetate, the organic phase is combined and washed with saturated common salt solution. After drying over sodium sulfate and concentration by evaporation in a vacuum, the residue obtained this way is chromatographed on aluminum oxide (Merck, step III, neutral) with a mixture of ethyl acetate/hexane. 10.2 g of 17-(prop-1-inyl)-5alpha, 10alpha-epoxy-3,3-(2,2-dimethyltrimethylenedioxy)-9(11)-estrene -17beta-ol is isolated as white foam.

IR (KBr): 2245 cm$^{-1}$ C—C triple bond.

b) 17-(prop-1-inyl)-11beta-(4-vinylphenyl-3,3-(2,2-dimethyltrimethylenedioxy)-9-estrene-5alpha,17beta-diol Table 3

EXAMPLE 2

17-(3-hydroxyprop-1-(Z)-enyl)-17beta-hydroxy-11beta-(4-vinylphenyl)-4,9-estradien-3-one a) production of the starting substrate for the Grignard addition 17-[3-(tetrahydropyran-2-yloxy)-prop-1-(Z)-enyl]-5alpha,10alpha-epoxy -3,3-(2,2-dimethyltrimethylenedioxy-9(11)-estrene-17beta-ol 20 g of 17-[3-(tetrahydropyran-2-yloxy)-prop-1-inyl]-5alpha,10alpha-epoxy -3,3-(2,2-dimethyltrimethylenedioxy-9(11)-estrene-17beta-ol is dissolved in 400 ml of ethanol and mixed with 40 ml of pyridine and 4 g of palladium/barium sulfate (10%). Next, hydrogenation is performed at normal pressure with hydrogen. After taking up an equivalent hydrogen, the catalyst is separated by filtration over celite, the filtrate is concentrated by evaporation and the residue is chromatographed on aluminum oxide (Merck, step II, neutral) with a mixture of ethyl acetate/hexane. 18.8 g of 17-[3-(tetrahydropyran-2-yloxy)-prop-1-(Z)-enyl]-5alpha,10alpha-epoxy-3,3-(2,2-dimethyltrimethylenedioxy)-9(11)-estrene-17beta-ol is isolated as white foam.

b) 17-[3-(tetrahydropyran-2-yloxy)-prop-1-(Z)-enyl]-11beta-(4-vinylphenyl)-3,3-(2,2-dimethyltrimethylenedioxy)-9-estren5alpha,17beta-diol
Table 3

EXAMPLE 3

17-(3-hydroxypropyl)-17alpha-hydroxy-13alpha-methyl-11beta-(4-isopropenylphenyl)-4,3-gonadien-3-one a) production of the substrate for the Grignard addition 17-[3-(tetrahydropyran-2-yloxy)-propyl]-13alpha-methyl-5alpha,10alpha-epoxy -3,3-(2,2-dimethyltrimethylenedioxy)-9(11)-gonene-17alpha-ol 5.1 g of 17-[3-(tetrahydropyran-2-yloxy)-prop-1-inyl]-13alpha-methyl-5alpha,10alpha-epoxy-3,3-[2,2-dimethyltrimethylenedioxy)-9,11-gonene-17alpha-ol is dissolved in 150 ml of tetrahydrofuran and mixed with 2.55 g of tris-(triphenylphosphine)-rhodium-(1)-chloride. Next it is hydrogenated with hydrogen at normal pressure for 20 hours. Next the reaction mixture is concentrated by evaporation and the residue is chromatographed on aluminum oxide (Merck, step III, neural) with a mixture of ethyl acetate/hexane. 4.9 g of the desired compound is isolated as white foam.

b) 17-[3-(tetrahydropyran-1-yloxy)-propyl]-13alpha-methyl-11beta-(4-isopropenylphenyl) -3,3-(2,2-dimethyltrimethylenedioxy)9-gonene-5alpha,17alpha-diol
Table 3

EXAMPLE 4

17-(3-hydroxypropyl)-17alpha-hydroxy-13alpha-methyl-11beta-(4-ethylphenyl)-4,9-gonadien-3-one a) The substrate described in example 3a is used as starting product for the Grignard addition.

b) 17-[3-(tetrahydropyran-1-yloxy)-propyl]-13alpha-methyl-11beta-(4-ethylphenyl) -3,3-(2,2-dimethyltrimethylenedioxy)-9-gonene-5alpha,17alpha-diol
Table 3

EXAMPLE 5

17-(3-hydroxypropyl)-17alpha-hydroxy-13alpha-methyl-11beta-(4-vinylphenyl)-4,9-gonadien-3-one a) The substrate described in example 3a is also used as the starting product for the Grignard addition.

b) 17-[3-(tetrahydropyran-2-yloxy)-propyl]-13alpha-methyl-11beta-(4-vinylphenyl) -3,3-(2,2-dimethyltrimethylenedioxy)-9-gonene-5alpha,17alpha-diol
Table 3

EXAMPLE 6

See Example 8

17-hydroxy-17-(3-hydroxy-(Z)-prop-1-enyl)-11beta--(4-(3-thienyl)-phenyl)-4,9-estradien -3-one (Table 2)

a) The substrate described in example 2a is used as the starting product for the Grignard addition with 1-chloro-4-(3-thienyl)-benzene (preparation analogous to lit: Tetrahedron Letters 27, 4407 (1986).

b) 3,3-(2,2-dimethyltrimethylenedioxy)-17-(3-tetrahydropyran-2-yloxy)-prop-(Z)   -1-enyl]-11beta-[4-(3-thienyl)phenyl]-estr-9-ene-5alpha,17beta-diol
Table 3

EXAMPLE 7

17-hydroxy-17-(3-hydroxyprop-(Z)-1-enyl)-11beta--(4-(3-pyridyl)-phenyl)-4,9-estradien -3-one (Table 2)

a)3,3-(2,2-dimethyltrimethylenedioxy)-17-[3-(tetrahydropyran-2-yloxy)-prop-(Z)-1-enyl]-11beta-(4-tri-n-butylstannylphenyl)-estr-9-ene-5alpha,17beta-diol 30.6 mg of 1,4-bis-tri-n-butyl tin benzene (preparation analogous to lit: Chem. Ber. [Chemical Reports] 87,1255(1954) is placed under protective gas in 120 ml of absolute tetrahydrofuran at −78° C. and mixed drop by drop with 29 ml of a 1.6M solution of n-butyllithium in hexane. It is restirred for 2 hours at −78° C. and mixed with 2.0 g of copper(I)cyanide. After 30 minutes, a solution of 4.0 g of the compound described in example 2 is instilled in 10 ml of absolute tetrahydrofuran. After the addition, the mixture is warmed to room temperature, restirred for 48 hours and then poured over ice water.

The aqueous phase is extracted with ethyl acetate, the organic phases are combined and washed with saturated common salt solution. After drying over sodium sulfate and concentration by evaporation in a vacuum, the residue obtained this way is chromatographed on silica gel with a mixture of ethyl acetate/hexane/triethylamine. 3.5 g of the compound above is obtained.

1H-NMR(CDCl$_3$+d$_5$-pyridene) δ=0.50 (s,3H,18-H). 0.86(s,3H,acetal-Mo),0.88, 0.90, 0.92(3t,9H,Me), 1.05(s,3H,acetal-Mo),3.40-3.59(m,4H,acetal-CH2), 4.26(d,J=7Hz,1H,11alpha,4.75(m,1H,H-THP-ether), 5.52-5.82(m,2H,H-olefin..C-20 and C-21), 7.15,7.30 (AA'BB'-system,J=9Hz,4H,Ar-H).

b)3,3-(2,2-dimethyltrimethylenedioxy)-11beta-[4-(3-pyridyl)phenyl]-17-[3-(tetrahydropyran-2-yloxy)-prop-(Z)-1-enyl]-estr-9-ene-5alpha, 17beta--diol (Table 4)
Example 8 (see example 6)
17-hydroxy-17alpha-(3-hydroxy-(Z)-prop-1-enyl)-11beta--[4-(3-thienyl)-phenyl]-4,9-estradien -3-one (Table 2).

a) The substrate described in example 7a is used as the starting product for the coupling according to general directions B).

b)3,3-(2,2-dimethyltrimethylenedioxy)-17-[3-(tetrahydropyran-2-yloxy)-prop-(Z)-1-enyl]-11beta-[4-(3-thienyl)-phenyl]-estr-9-ene-5alpha,17beta-diol (Table 4)

The compound from example 6 is identical to the one from example 8.

EXAMPLE 9

17-hydroxy-17alpha (3-hydroxy-(Z)-prop-1-enyl)-11beta-[4-(3-furyl)-phenyl]-4,9-estradien-3-one (Table 2)

a) The substrate described in example 7a is used as the starting product for the coupling according to general directions B.

b)   3,3-(2,2-dimethyltrimethylenedioxy)-17-[3-(tetrahydropyran-2-yloxy)-prop-(Z)-1-enyl]-11beta-[4-(3-furyl)-phenyl]-estr-9-ene-5alpha,17beta-diol (Table 4)

EXAMPLE 10

17-hydroxy-17alpha(3-hydroxyprop-(Z)-1-enyl]-11beta-[4-(3-thiazolyl)-phenyl]-4,9-estradien-3-one (Table 2)

a) The substrate described in example 7a is used as the starting product for the coupling according to general directions B.

b) 3,3-(2,2-dimethyltrimethylenedioxy)-17-[3-(tetrahydropyran-2-yloxy)-prop-(Z)-1-enyl]-11beta-[4-(2-thiazolyl)-phenyl]-estr-9-ene-5alpha,17beta-diol (Table 4)

EXAMPLE 11

17-hydroxy-17beta-(3-hydroxypropyl)-13alpha-methyl-11beta-[4-(3-pyridyl)-phenyl-1-4,9-gonadien-3-one (Table 2).

a) 11beta-(4-bromophenyl)-3,3-(2,2-dimethyltrimethylenedioxy)-13alpha-methyl-17-[3-(tetrahydropyran-2-yloxy)-propyl]-9-gonene-5alpha,17alpha-diol 3.16 g of magnesium chips are placed under protective gas in 15 ml of absolute tetrahydrofuran and mixed with 0.1 ml of dibromoethane. After completed reaction, a solution of 30.7 g of 1,4-dibromobenzene in 500 ml of absolute tetrahydrofuran is instilled slowly. After complete reaction (30 minutes at 40° C., the Grignard solution is cooled to 0° C and mixed with 160 mg of copper-I-chloride. Next, a solution of 5.6 g of the epoxide in 110 ml of absolute tetrahydrofuran described in example 3a is instilled. The reaction mixture is worked up as described in the general directions. After column chromatography, 6.6 g of the above compound was obtained.

b) 3,3-(2,2-dimethyltrimethylenedioxy)-13alpha-methyl-17-[3-(tetrahydropyran-2-yloxy)-propyl]-11beta-(4-tri-n-butylstannylphenyl)-9-gonene-5alpha,17alpha-diol 6.27 g of the compound produced under a) is placed under protective gas in 180 ml of absolute dioxane, mixed with 15 ml of hexabutylditin, 625 mg of bis-(triphenylphosphine)-palladium-II-chloride and 2.5 g of tetrabutylammonium chloride and then refluxed for 2 hours. After filtration over celite, concentration by evaporation in a vacuum is performed and the residue is chromatographed on aluminum oxide with a mixture of ethyl acetate/hexane. 4.8 g of the above compound is obtained.

c) 3,3-(2,2-dimethyltrimethylenedioxy-13alpha-methyl-11beta[4-(3-pyridyl)-phenyl]-17-[3-tetrahydropyran-2-yloxy)-propyl]-9-gonene-5alpha,17alpha-diol (Table 4)

EXAMPLE 12

17-hydroxy-17beta-(3-hydroxypropyl)-13alpha-methyl-11beta[4-(4-cyanophenyl)-phenyl]-4,9-gonadien-3-one (Table 2)

a) The substrate described in example 11b is used as the starting product for the coupling according to general directions B.

b) 3,3-(2,2-dimethyltrimethylenedioxy)-13alpha-methyl-11beta-[4-(4-cyanophenyl)-phenyl]-17-[3-(tetrahydropyran-2-yloxy)propyl]-9-gonene-5alpha,17alpha-diol (Table 4)

EXAMPLE 13

17-hydroxy-17beta-(3-hydroxypropyl)-13alpha-methyl-11beta-[4-(5-pyrimidyl)-phenyl]-4,9-gonadien-3-one (Table 2)

a) The substrate described in example 11b is used as the starting product for the coupling according to general directions B.

b) 3,3-(2,2-dimethyltrimethylenedioxy)-13alpha-methyl-11beta-[4-(5-pyrimidyl)-phenyl]-17-[3-(tetrahydropyran-2-yloxy)propyl]-9-gonene-5alpha,17alpha-diol (Table 4)

EXAMPLE 14

See Example 17

17-hydroxy-17beta-(3-hydroxypropyl)-13alpha-methyl-11beta-[4-(3-thienyl)-phenyl]-4,9-gonadien-3-one (Table 2).

a) The substrate described in example 11a is used for the starting product for the coupling according to general directions C.

b) 3,3-(2,2-dimethyltrimethylenedioxy)-13alpha-methyl-17-[3-(tetrahydropyran-2-yloxy)-propyl]-11beta-[4-(3-thienyl)-phenyl]-9-gonene-5alpha,17alpha-diol (Table 5)

EXAMPLE 15

17-hydroxy-17beta-(3-hydroxypropyl)-13alpha-methyl-11beta-[4-(3-furyl)-phenyl]-4,9-gonadien-3-one (Table 2).

a) The substrate described in example 11a is used as the starting product for the coupling according to general directions C.

b) 3,3-(2,2-dimethyltrimethylenedioxy)-13alpha-methyl-11beta-[4-(3-furyl)-phenyl]-17-[3-(tetrahydropyran-2 yloxy)propyl]-9-gonene-5alpha, 17alpha-diol (Table 5)

EXAMPLE 16

17-hydroxy-17alpha-(3-hydroxypropyl)-13alpha-methyl-11beta-[4-(2-thiazolyl)-phenyl]-4,9-gonadien-one (Table 2)

a) The substrate described in example 11a is used as the starting product for the coupling according to general directions C.

b) 3,3-(2,2-dimethyltrimethylenedioxy)-13alpha-methyl-11beta-[4-(2-thiazolyl)-phenyl]-17-[3-(tetrahydropyran-2-yloxy)propyl]-9-gonene-5alpha, 17alpha-diol (Table 5).

EXAMPLE 17 (SEE EXAMPLE 14)

17-hydroxy-17beta-(3-hydroxypropyl)-13alpha-methyl-11beta-[4-(3-thienyl)-phenyl]-4,9-gonadien-3-one (Table 2). The compound of example 14 is identical to the one from example 17.

a) 3,3-(2,2-dimethyltrimethylenedioxy)-11beta-(4-tri-n-butylstannylphenyl)-estr-9-ene-5alpha,17beta-diol.

From 10 g of 3,3-(2,2-dimethyltrimethylenedioxy)-5alpha,10alpha-epoxy-estr-9(11)-en-17beta-ol there is obtained, as described under example 7a, 5.1 g of the above compound. 1-H-NMR(CDCl3+Pyd5) $\delta=0.38$ (s,3H,1S-H), 0.87(s,3H, acetal-Me), 0.89, 0.91, 0.93(3t,9H,Me), 1.05(s,3H,acetyl-Me),3.42-3.67(m,5H, 17-H and acetal-CH2), 4.22(d,J=7Hz,1H,11alpha-H), 4.40(s. wide, 1H,OH), 7.17, 7.31(AA'BB' system, J=9Hz,4H, Ar-H).

b) 3,3-(2,2-dimethyltrimethylenedioxy)-11beta-[4-(3-thienyl)-phenyl]-estr-9-ene-5alpha,17beta-diol From 5.1 g of the compound described under 17a, 2.8 g of the above compound were obtained according to general directions a.

c) 3,3-(2,2-dimethyltrimethylenedioxy)-5alpha-hydroxy-11beta-[4-(3-thienyl)-phenyl]-estr-9-en-17-one.

From 2.8 g of the compound described under 17b, 1.6 g of aluminum triisopropylate and 11.6 ml of cyclohexanone in 60 ml of absolute toluene, after 3 hours of heating on the water separator according to the usual working up and purification by column chromatography, 2.05 g of the above compound is obtained.

d) 3,3-(2,2-dimethyltrimethylenedioxy)-5alpha-hydroxy13alpha-methyl-11beta-[4-(3-thienyl)-phenyl]-9-gonen-17-one From 2.05 g of the compound described under 17c in 600 ml of absolute dioxane, after 10 minutes of irradiation at room temperature with a mercury high pressure lamp (Philips HPK 125) and chromatographic purification, 840 mg of the above compound is obtained.

e) 3,3-(2,2-dimethyltrimethylenedioxy)-13alpha-methyl-17-[3-(tetrahydropyran-2-yloxy)-1-propinyl ]-11beta-(4-(3-thienyl)phenyl]-9-gonene-5alpha,17alpha-diol From 840 mg of the compound described under 17d in 20 ml of absolute tetrahydrofuran, 4.52 g of 2-(propargyloxy)tetrahydropyran in 80 ml of absolute tetrahydrofuran and 19 ml of a 1.6M solution of n-butyllithium in hexane, after chromatographic purification, 370 mg of the above compound is obtained.

f) 3,3-(2,2-dimethyltrimethylenedioxy)-13alpha-methyl-17-[3-(tetrahydropyran-2-yloxy) -propyl]-11beta-[4-(3-thienyl)-phenyl]-9-gonene-5alpha,17alpha-diol.

From 370 mg of the compound produced under 17e, as described under example 3a, 310 mg of the above compound is obtained.

EXAMPLE 18

3,3-(2,2-dimethyltrimethylenedioxy)-13alpha-ethyl-5alpha-hydroxy-11beta-[4-(3-thienyl)-phenyl]-9-gonen-17-one From 2.9 g of 3,3-(2,2-dimethyltrimethylenedioxy)-5alpha-hydroxy-18-methyl-11beta-[4-(3-thienyl)-phenyl]-estr-9-en-17-one (preparation analogous to example 17) there is obtained, as described under 17d, after chromatographic purification, 970 mg of the above compound.

1H-NMR(CDCl3+Py-d5) δ=0.84(s.3H,acetal-Me), 0.88(t,3H,18-Me), 1.02 (s,3H,acetal-Me),3.35-3.56(m,4H,acetal-CH2), 3.80(m,1H,11alpha-H),4.42(s, wide, 1H,OH), 7.13, 7.50 (AA'BB'-system, J=9Hz,4H,Ar-H), 7.38-7.45(m,3H,Ar-H).

EXAMPLE 19

17beta-hydroxy-18-methyl-17-(1-propinyl)-11beta-[4-(3-thienyl)-phenyl]-estra-4,9-dien-3-one (Table 2).

1H-NMR(CDCl3) δ=0.31(t,J=7Hz,3H,18-Me), 1.91(s,3H,C≡C-Me), 4.45(d,J=7Hz,1H,11alpha-H), 5.78(s,1H,4-H), 7.21, 7.50 (AA'BB' system, J=9Hz, 4H,Ar-H), 7.34–7.46(m,3H,Ar-H).

a) The starting material in example 18 is used as the starting product for the propinylation.

b) 3,3-(2,2-dimethyltrimethylenedioxy)-18-methyl-17-(1-propinyl)-11beta-[4-(3-thienyl)-phenyl]-estr-9-ene-5alpha, 17beta-diol From 1.91 g of 3,3-(2,2-dimethyltrimethylenedioxy-5alpha-hydroxy-18-methyl-11beta-[4-(3-thienyl)-phenyl]-estr-9-en-17-one in 40 ml of absolute tetrahydrofuran, 180 ml of a tetrahydrofuran solution saturated with propine and 24 ml of a 1.6M solution of butyllithium in hexane, after chromatographic purification, 1.47 g of the compound above is obtained.

TABLE 2

| Beispiel | Ansatz x [g] y [ml] | Reaktionsparameter t [°C.]  z [min] | | Ausbeute a [g] | $[α]_D^{20}$ |
|---|---|---|---|---|---|
| 1 | 10    100 Steroid 1b | 50 | 60 | 6.54 | 131 (CHCl3; c = 0.053) Steroid Beispiel 1 |
| 2 | 15    150 Steriod 2b | 50 | 60 | 6.25 | 218 (CHCl3: c = 0.505) Steroid Beispiel 2 |
| 3 | 5    50 Steroid 3b | 50 | 180 | 1.73 | 380 (CHCl3: c = 0.515) Steroid Beispiel 3 |
| 4 | 1.4    35 Steroid 4a | 50 | 60 | 0.68 | 349 (CHCl3: c = 0.510) Steroid Beispiel 4 |
| 5 | 1.1    28 Steroid 5a | 50 | 60 | 0.41 | 419 (CHCl3: c = 0.500) Steroid Beispiel 5 |

| Bsp. | Ansatz x [g] y [ml] | Reaktionsparameter t [°C.]  z [min] | | Ausbeute a [g] | $[α]_D^{20}$ CHCl3 |
|---|---|---|---|---|---|
| 6 | 1.4    15 Steroid 6b | 50 | 60 | 0.54 | 249 c = 0.52 Steroid Beispiel 6 |
| 7 | 0.74    10 Steroid 7b | 50 | 40 | 0.30 | 208 c = 0.505 Steroid Beispiel 7 |
| 8 | 1.3    14 Steroid 8b | 50 | 40 | 0.40 | 250 c = 0.52 Steroid Beispiel 8 |
| 9 | 1.2    15 Steroid 9b | 50 | 45 | 0.53 | 228 c = 0.505 Steroid Beispiel 9 |
| 10 | 1.4    18 Steroid 10b | 50 | 30 | 0.68 | 297 c = 0.505 Steroid Beispiel 10 |
| 11 | 0.60    8 Steroid 11c | 50 | 40 | 0.27 | 395 c = 0.51 Steroid Beispiel 11 |
| 12 | 0.86    11 Steroid 12b | 50 | 45 | 0.35 | 438 c = 0.51 Steroid Beispiel 12 |
| 13 | 0.80    12 Steroid 13b | 50 | 30 | 0.30 | 390 c = 0.51 Steroid Beispiel 13 |
| 14 | 1.0    15 Steroid 14b | 50 | 45 | 0.46 | 424 c = 0.505 Steroid Beispiel 14 |
| 15 | 1.3    19 Steroid 15b | 50 | 45 | 0.50 | 389 c = 0.51 Steroid Beispiel 15 |
| 16 | 0.80    9 Steroid 16b | 50 | 45 | 0.34 | 431 c = 0.5 Steroid Beispiel 16 |
| 17 | 0.31    6 Steroid 17f | 30 | 30 | 0.11 | 421 c = 0.51 Steroid Beispiel 17 |

TABLE 2-continued

| | | | | | | | |
|---|---|---|---|---|---|---|---|
| 19 | 0.32 | 6 | 50 | 30 | 0.14 | — | |
| | Steroid 19b | | | | | Steroid Beispiel 19 | |

Key:
[Beispiel] = example
[Ansatz] = ingredients
[Reaktionsparameter] = reaction parameters
[Ausbeute] = yield

TABLE 3

| | Ansatz | | | Halogenaromat | Ausbeute | | |
|---|---|---|---|---|---|---|---|
| Beispiel | Epoxid EP | [mmol] | [g] | (X = Br,I) | Addukt Y | [mmol] | [g] |
| 1 | Steroid 1a | 24 | 9.9 | 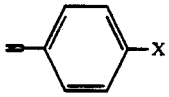 | Steroid 1b | 20.3 | 10.5 |
| 2 | Steroid 2a | 29.14 | 15 | 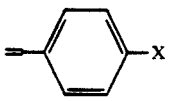 | Steroid 2b | 26.18 | 16.2 |
| 3 | Steroid 3a | 14.52 | 7.5 |  | Steroid 3b | 10.82 | 6.67 |
| 4 | Steroid 3a | 2.75 | 1.42 | 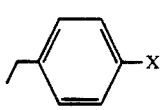 | Steroid 4a | 2.33 | 1.45 |
| 5 | Steroid 3a | 2.03 | 1.05 | 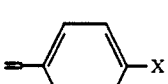 | Steroid 5a | 1.95 | 1.21 |
| 6 | Steroid 2a | 5.13 | 3.0 | 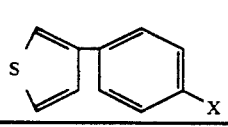 | Steroid 6b | 2.07 | 1.4 |

Key:
[Beispiel] = example
[Ansatz] = ingredients
[Epoxid] = epoxide
[Halogenaromate] = haloaromate
[Ausbeute] = yield
[Addukt] = adduct

TABLE 4

| | Ansatz | | | Halogenaromat | Ausbeute | | |
|---|---|---|---|---|---|---|---|
| Bsp. | Stannan X | [mmol] | [g] | (X = Br,I) | Addukt Y | [mmol] | [g] |
| 7 | Steroid 7a | 2.36 | 2.08 | 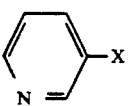 | Steroid 7b | 1.10 | 0.74 |
| 8 | Steroid 7a | 2.27 | 2.00 | 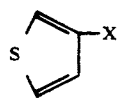 | Steroid 8b | 1.93 | 1.30 |
| 9 | Steroid 7a | 2.31 | 2.04 | 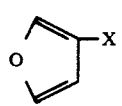 | Steroid 9b | 1.82 | 1.20 |

TABLE 4-continued

| Bsp. | Ansatz | | | Halogenaromat (X = Br.I) | Ausbeute | | |
|---|---|---|---|---|---|---|---|
| | Stannan X | [mmol] | [g] | | Addukt Y | [mmol] | [g] |
| 10 | Steroid 7a | 2.51 | 2.21 | (N, S thiazole)-X | Steroid 10b | 2.07 | 1.40 |
| 11 | Steroid 11b | 1.84 | 1.63 | (pyridine)-X | Steroid 11c | 0.89 | 0.60 |
| 12 | Steroid 11b | 2.26 | 2.00 | NC-(phenyl)-X | Steroid 12b | 1.23 | 0.86 |
| 13 | Steroid 11b | 3.31 | 2.93 | (pyrimidine)-X | Steroid 13b | 1.19 | 0.80 |

Key:
[Bsp.] = example
[Ansatz] = ingredients
[Stannan] = stannane
[Halogenaromat] = haloaromate
[Ausbeute] = yield
[Addukt] = adduct

TABLE 5

| Bsp. | Ansatz | | | Heteroarylstannan (X = SnBu3) | Ausbeute | | |
|---|---|---|---|---|---|---|---|
| | Halogen X | [mmol] | [g] | | Addukt Y | [mmol] | [g] |
| 14 | Steroid 11a | 2.22 | 1.50 | (thiophene)-X | Steroid 14b | 1.53 | 1.0 |
| 15 | Steroid 11a | 2.22 | 1.50 | (furan)-X | Steroid 15b | 1.97 | 1.3 |
| 16 | Steroid 11a | 1.48 | 1.00 | (N, S thiazole)-X | Steroid 16b | 1.18 | 0.8 |

[Bsp.] = example
[Ansatz] = ingredients
[Heteroarylstannan] = heteroarylstannane
[Ausbeute] = yield
[Addukt] = adduct The preceding examples can be repeated with similar success by substituting the generically or specifically described reactants and/or operating conditions of this invention for those used in the preceding examples.

From the foregoing description, one skilled in the art can easily ascertain the essential characteristics of this invention, and, without departing from the spirit and scope thereof, can make various changes and modifications of the invention to adapt it to various usages and conditions.

We claim:
1. 13-alkyl-11beta-phenyl-gonanes of formula I

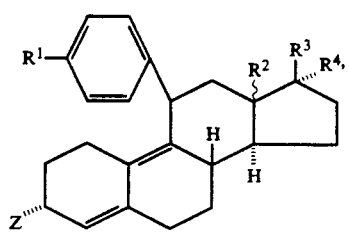

in which
Z is an oxygen atom or the hydroxyimino grouping N~OH,

R¹ is a heteroaryl radical selected from the group consisting of 3-thienyl, 3-furyl, 3-pyrrolyl, 3-pyridyl, 4-pyridyl, 5-pyrimidine, 4-pyridazine, and pyrazine and, optionally, the heteroaryl radical of R¹ is substituted by one or more halogen radicals and/or one or more alkyl radicals with 1 to 3 carbon atoms, and R² stand for an alpha- or a beta-position methyl or ethyl radical, and if R² is in alpha position,

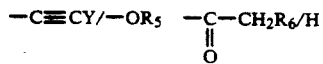

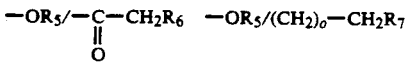

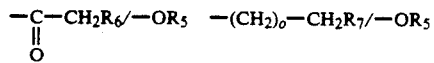

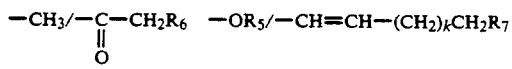

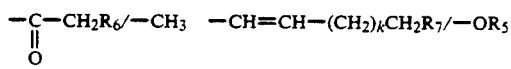

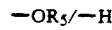

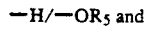

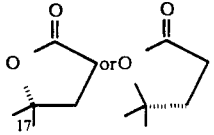

and if R² is in beta position,
R³/R⁴ mean

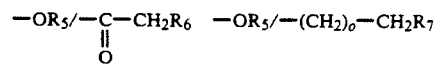

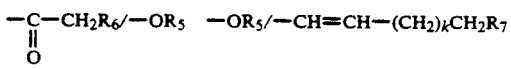

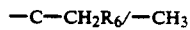

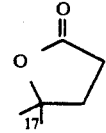

with $R_5$ meaning a hydrogen atom or an acyl radical with 1 to 4 carbon atoms,

Y meaning a hydrogen, chlorine, fluorine, iodine or bromine atom, an alkyl, hydroxyalkyl, alkoxyalkyl or acyloxyalkyl group each with 1 to 4 carbon atoms in the alkyl or acyl radical, $R_6$ meaning a hydrogen atom, a hydroxyl group, an alkyl, O-alkyl, or O-acyl group each with 1 to 4 carbon atoms, o means 0, 1, 2 or 3, $R_7$ meaning a hydroxy or cyanide radical, an O-alkyl or O-acyl group each with 1 to 4 carbon atoms and k meaning 0, 1 or 2.

2. 17-hydroxy-17beta-(3-hydroxypropyl)-13alpha-methyl-11beta-[4-(3-thienyl)-phenyl]-4,9-gonadien-3-one 17-hydroxy-17alpha-(3-hydroxypropyl)-13alpha-methyl-11beta-[4-(3-thienyl)-phenyl]-4,9-gonadien-3-one 17-hydroxy-17beta-(3-hydroxypropyl)-13alpha-methyl-11beta-[4-(2-thienyl)-phenyl]-4,9-gonadien-3-one 17-hydroxy-17alpha-(3-hydroxypropyl)-13alpha-methyl-11beta-[4-(2-thienyl)-phenyl]-4,9-gonadien-3-one 11beta-[4-(2-furyl)-phenyl-17-hydroxy-17beta-(3-hydroxypropyl)-13alpha-methyl-4,9-gonadien-3-one 11beta-[4-(2-furyl)-phenyl]-17-hydroxy-17alpha-(3-hydroxypropyl)-13alpha-methyl-4,9-gonadien-3-one 11beta-[4-(3-furyl)-phenyl]-17-hydroxy-17beta-(3-hydroxypropyl)-13alpha-methyl-4,9-gonadien-3-one 17-hydroxy-17beta-(3-hydroxypropyl)-13alpha-methyl-11beta-[4-(2-pyridyl)-phenyl]-4,9-gonadien-3-one 17-hydroxy-17alpha-(3-hydroxypropyl)-13alpha-methyl-11beta-[4-(2-pyridyl)-phenyl]-4,9-gonadien-3-one 17-hydroxy-17beta-(3-hydroxypropyl)-13alpha-methyl-11beta-[4-(3-pyridyl)-phenyl]-4,9-gonadien-3-one 17-hydroxy-17alpha-(3-hydroxypropyl)-13alpha-methyl-11beta-[4-(3-pyridyl)-phenyl]-4,9-gonadien-3-one 17-hydroxy-17beta-(3-hydroxypropyl)-13alpha-methyl-11beta-[4-(4-pyridyl)-phenyl]-4,9-gonadien-3-one 17-hydroxy-17-alpha-(3-hydroxypropyl)-13alpha-methyl-11beta-[4-(4-pyridyl)-phenyl]-4,9-gonadien-3-one 17-hydroxy-17beta-(3-hydroxypropyl)-13alpha-methyl-11beta-[4-(2-thiazolyl)-phenyl]-4,9-gonadien-3-one 17-hydroxy-17alpha-(3-hydroxypropyl)-13alpha-methyl-11beta-[4-(2-thiazolyl)-phenyl],4,9-gonadien-3-one 17-hydroxy-17alpha-(3-hydroxyprop-(Z)-1-enyl)-11beta-[4-(3-thienyl)-phenyl]-4,9-estradien-3-one.

3. 13-alkylgonanes according to claim 1, wherein the heteroaryl radical of R¹ is substituted by a chlorine or bromine atom.

4. 13-alkylgonanes according to claim 1, wherein the heteroaryl radical of R¹ is substituted by an alkyl radical with 1 to 3 carbon atoms.

5. 17-hydroxy-17 alpha-(3-hydroxypropyl)-13 alphamethyl-11beta-[4-(3-furyl)-phenyl]-4,9-estradien-3-one.

6. A pharmaceutical antigestagenic preparation comprising a pharmaceutically acceptable carrier and a compound according to claim 1.

7. A pharmaceutical antigestagenic preparation comprising a pharmaceutically acceptable carrier and a compound according to claim 2.

8. A method of effecting antigestagenic activity, comprising administering an effective amount of a compound according to claim 1.

9. A method of effecting antigestagenic activity, comprising administering an effective amount of a compound according to claim 2.

* * * * *

UNITED STATES PATENT AND TRADEMARK OFFICE
CERTIFICATE OF CORRECTION

PATENT NO. : 5,273,971
DATED : December 28, 1993
INVENTOR(S) : Stefan SCHOLZ ET AL.

It is certified that error appears in the above-indentified patent and that said Letters Patent is hereby corrected as shown below:

In the abstract, formula (I): Delete the formula and insert the following new formula: --

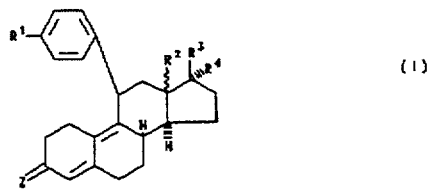

(I)

--.

Column 24, formula (I): Delete the formula and insert the following new formula: --

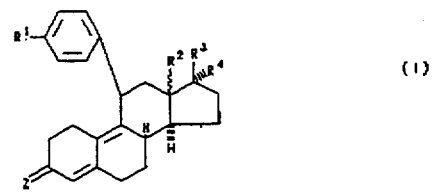

(I)

Signed and Sealed this

Twenty-ninth Day of August, 1995

Attest:

BRUCE LEHMAN

*Attesting Officer*     *Commissioner of Patents and Trademarks*